United States Patent [19]
Eikmeier et al.

[11] Patent Number: 5,162,238
[45] Date of Patent: Nov. 10, 1992

[54] TEST CARRIER FOR ANALYSIS OF A LIQUID SAMPLE

[75] Inventors: Henio Eikmeier, Lorsch, Fed. Rep. of Germany; Helmut Freitag, Indianapolis, Ind.; Karin Münter, Mannheim, Fed. Rep. of Germany; Klaus Pollmann, Indianapolis, Ind.; Hans-Erich Wilk, Lorsch; Johannes Winkle, Hirschberg-Leutershausen, both of Fed. Rep. of Germany

[73] Assignee: Boehringer Mannheim GmbH, Mannheim, Fed. Rep. of Germany

[21] Appl. No.: 275,409

[22] Filed: Nov. 23, 1988

[30] Foreign Application Priority Data

Nov. 28, 1987 [DE] Fed. Rep. of Germany ....... 3740471

[51] Int. Cl.$^5$ .................... G01N 33/549; G01N 21/00
[52] U.S. Cl. ...................................... 436/532; 422/56; 435/7.5
[58] Field of Search ............... 422/56, 57; 436/532; 435/7.5

[56] References Cited

U.S. PATENT DOCUMENTS

| | | |
|---|---|---|
| 3,652,761 | 3/1972 | Weetall .............................. 436/525 |
| 4,219,335 | 8/1980 | Ebersole .............................. 422/63 |
| 4,312,834 | 1/1982 | Vogel et al. ......................... 435/4 |
| 4,560,504 | 12/1985 | Arnold . | |
| 4,657,739 | 4/1987 | Yasuda et al. . | |
| 4,820,489 | 4/1989 | Rothe et al. ........................ 422/58 |
| 4,916,056 | 4/1990 | Brown, III et al. ................ 436/531 |
| 5,002,884 | 3/1991 | Kobayashi et al. ................ 436/532 |

FOREIGN PATENT DOCUMENTS

| | | |
|---|---|---|
| 0016387 | 10/1980 | European Pat. Off. . |
| 0133895 | 3/1985 | European Pat. Off. . |
| 0200381 | 11/1986 | European Pat. Off. . |
| 3343695 | 6/1984 | Fed. Rep. of Germany . |
| 1420916 | 1/1976 | United Kingdom . |

OTHER PUBLICATIONS

The Condensed Chemical Dictionary, p. 322, ©1981 Defn. of "Diatomaceous earth".

*Primary Examiner*—David L. Lacey
*Assistant Examiner*—Abanti B. Singla
*Attorney, Agent, or Firm*—Felfe & Lynch

[57] ABSTRACT

The present invention provides a test carrier for the analysis of a sample liquid with a test layer which contains a ligand fixed to to carrier particles, which ligand reacts with a component of the sample liquid, the test layer having a three-dimensional open structure which is so porous that the sample liquid with the component can penetrate into it, the carrier particles being arranged in the layer in such a manner that the ligand, upon pentration of the sample liquid, comes into contact with the component of the sample, wherein the carrier particles consist of an inorganic material, on the surface of which reactive organic groups are covalently bound as coupling groups, and the ligand is covalently bound to the coupling groups. The present invention also provides processes for the production of such a test carrier and a method for using it.

14 Claims, 1 Drawing Sheet

TEST CARRIER FOR ANALYSIS OF A LIQUID SAMPLE

The present invention is concerned with a test carrier useful of a sample liquid comprising a test layer which contains a ligand fixed on to carrier particles, which ligand reacts with a component of the sample liquid, the test layer having a three dimensional open structure which is so porous that the sample liquid with the component can penetrate into it, the carrier particles being arranged in the layer in such a manner that the ligand, upon penetration of the sample liquid, comes into contact with the component of the sample. The present invention is also concerned with processes for the production of this test carrier and uses thereof.

Recently, so-called "carrier-bound test devices" have been used in qualitative and quantitative analytical determinations to an increasing extent. In these test devices, reagents are embedded in one or more test layers of a solid test carrier which is then brought into contact with a sample. The reaction of the sample and reagents leads to a detectable signal which is usually a color change, and this can be evaluated visually or with the help of apparatus, such as a reflection photometer. Test carrier analysis is used, in particular, for the analysis of body fluids, such as blood or urine, and also in medical diagnosis, e.g.

Test carriers are frequently constructed as test strips. These consist essentially of a longitudinal base layer of synthetic resin material with test layers applied thereto. However, test carriers are also known which are formed as quadratic or rectangular platelets.

Immunological determinations are of special importance in medical analysis. Generally, these are characterized by highly specific binding reactions between immunological binding components, especially between antigens and antibodies or between haptens and antibodies. When immunological determinations are carried out using test carriers, it is frequently necessary to fix one of the binding components within a test layer structure. Difficult criteria must be satisfied in such cases.

The present invention is directed especially to test carriers for such immunological determinations but it can also be used in other cases in which ligands of any type are embedded in carrier-fixed form in a three-dimensional open test layer structure.

A survey of known test layer structures for immunological determinations is to be found, for example, in U.S. Pat. No. 4,613,567. According to this application, easy penetration of the sample into the test layer and the necessary free contact can be achieved by the use of an appropriate open-pored porous structure. Membrane filters, fabrics, filter papers and glass fiber filter layers are mentioned as appropriate materials. The ligands can be bound to small polymer spheroids which are arranged in the porous structure. For this purpose, functional groups are formed by etching the polymer with an acid.

In U.S. Pat. No. 4,258,001 a test layer structure is described, inter alia, for immunological use, in which the polymer spheroids are stuck together with the help of an adhesive in the form of an organic polymer different from the polymer of the particles, to give a three-dimensional lattice structure. The open porosity of the structure thus obtained is highly emphasized.

According to the present invention, there is provided a test carrier for the analysis of a sample liquid with a test layer which contains a ligand fixed on to carrier particles, which ligand reacts with a component of the sample liquid, the test layer having a three-dimensional open structure which is so porous that the sample liquid with the component can penetrate into it, the carrier particles being arranged in the layer in such a manner that the ligand, upon penetration of the sample liquid, comes into contact with the component of the sample, wherein the carrier particles consist of an inorganic material, on the surface of which reactive organic groups are covalently bound as coupling groups, and the ligand is either covalently bound to the coupling group or the ligand is covalently bound to a bridging molecule which is bound, covalently, to the coupling group.

According to the present invention, the test layer is produced by a process involving at least three steps. In the first step, the ligand is fixed to the carrier particles with the help of coupling groups. In the second step, the particles are separated from the substances needed for fixing the reagent, for example by filtering, centrifuging or sedimentation. Finally, in the third step, the carrier particles are either incorporated into a previously present porous carrier matrix or the layer structure with the carrier particles is produced as a film which is opened by the addition of an opener in the form of particulate components.

Techniques for coupling ligands of various kinds such as, but not limited to antibodies, to solid surfaces are known for other purposes, such as the production of filling materials for chromatographic columns in order to purify immunological reagents. The reactive organic groups can, be, e.g., amine groups or carboxyl groups to which the ligand is coupled via an amide bond. Such a type of coupling for antibodies is described in several variants in U.S. Pat. No. 4,560,504. The technique is based on analogous processes for the binding of enzymes in organic carriers, such as are described in the articles by Howard H. Weetall "Enzymes immobilized on inorganic supports", Trends in Biotechnology, 1985, p. 276–280 and H. H. Weetal "Covalent coupling methods for inorganic support materials" in "Methods in Enzymology", Vo. XLIV, ed. K. Mosbach, pub. Academic Press, New York, San Franciso, London, 1976, pp. 134–149.

According to the present invention, the coupling groups are preferably produced on the surface of the inorganic particles via silanization reagents, such as 3-aminopropyltriethoxysilane, the silane groups of which are condensed onto the inorganic materials with ethanol split off in the condensation reaction.

One example of a material useful as a carrier particle is silicon dioxide particles such as silicon dioxide particles used as silica gels for chromatographic purposes. Titanium dioxide is an especially preferred particle substance.

In one preferred embodiment, the ligand is bound to the coupling groups via bridging molecules. The term "bridging molecules" designates organic molecules which are suitable for increasing the distance between the ligands and the surface of the particles. The bridging molecules must have at least two reactive organic groups, preferably near the ends of the molecules. One of the reactive organic groups covalently binds the coupling groups, and the other reactive organic group serves to covalently bind the ligands. Otherwise, the bridging molecules should be completely unreactive.

On the ligand side however, several reactive organic groups can be present for coupling on several ligands.

According to an especially preferred embodiment, the carrier particles have an average diameter of from 0.2 to 1μ, in which case titanium dioxide is especially preferred. The titanium dioxide particles consist of substantially homogeneous particles with a defined surface. Furthermore, they are pigmented. Due to this double function, a reduction of the layer thickness is obtained while the effect of the layer remains the same.

The present invention makes possible high and uniform loading of the test layer with the ligands. The test devices thus produced are extremely effective in analysis, and yet have smaller layer thicknesses as compared to known devices. The small layer thickness in turn, allows one to work with a very small amount of liquid sample.

The present invention also provides considerable advantages in the production techniques necessary to make the apparatus. In particular, the carrier particles can be contacted with organic solvents without their being damaged. Furthermore, they can be separated from the reagents needed for fixing the ligands by means of filtering, centrifuging or sedimentation rather easily.

The inorganic carrier particles can be incorporated in various sufficiently wide-pored matrix materials, such as are described, for example, in the above-mentioned U.S. Pat. No. 4,613,567. An especially preferred embodiment uses a test layer which is produced from a solution or dispersion of film-forming organic synthetic resins with the addition of an opener in the form of corpuscular components. In this regard, reference is made to U.S. Pat. No. 4,312,834. In contradistinction to fabrics and fleece, such a test layer is form-stable.

The opener preferably consists of inorganic particles with an average particle diameter of at least 5 μ, a preferred material being silicon dioxide. Diatomaceous earth is an especially preferred opener.

According to a further preferred embodiment of the present invention, a relatively small amount of film-forming organic synthetic resin is used, i.e., an amount which is, at most 25% by weight of the total amount of carrier particles and opener particles. The weight relationship between carrier particles and opener is preferably from 2:1 to 1:2. By these means optimum conditions with regard to the loading density with the ligand, easy accessibility of the fixed ligand for the sample entering the layer and small layer thickness are achieved in the three-component system of film, carrier particles and opener.

BRIEF DESCRIPTION OF THE DRAWINGS

The present invention will now be described in the following in more detail with reference to the embodiments illustrated in the accompanying drawings, in which

FIG. 1 explains the symbols used in FIG. 2. A silanization reagent 10 contains a silane group 11 and a reactive organic group 12 which can be, for example, a carboxyl group or an amino group and which serves as a coupling group.

Figure 1:
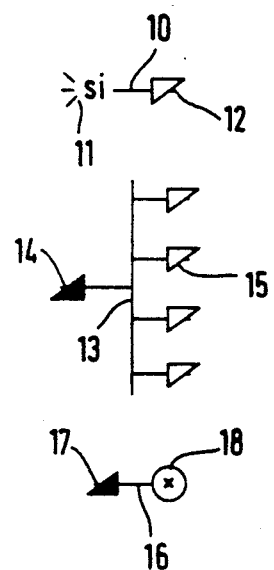
FIGS. 1 and 2 illustrates schematically the coupling of a ligand via bridge molecules to the carrier particles.

A bridge molecule indicated by 13 has a first reactive organic group 14 on the carrier particle side for coupling on to the complimentary group 12 of the silanization reagent, and on the ligand side, second reactive organic groups 15 for coupling to the ligand. At least one reactive organic group 15 must be present on the ligand side. Preferably, however, several such groups are present in order to allow the coupling on of several ligands to a bridge molecule and thus to increase the loading density.

The ligand 16 has a reactive organic group 17 which is complementary to the ligand-side reactive organic group or groups 15 of the bridge molecule 13 and thus makes possible covalent coupling therebetween. The end of the ligand 16 participating in the reaction is indicted by 18. When the ligand 16 is an antigen, 18 symbolizes the epitope to which an "appropriate" antibody can couple (antigenic determinant).

Figure 2:
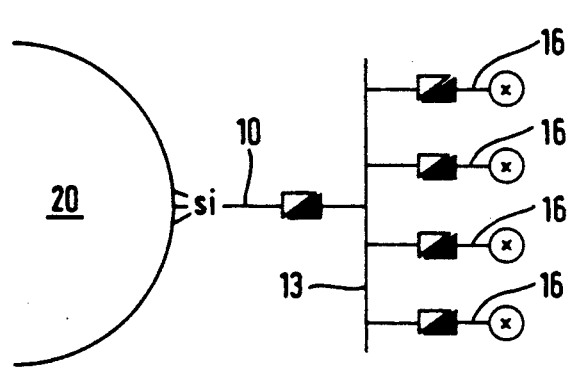

FIG. 2 shows an arrangement of the components on a carrier particle 20, for example a titanium dioxide particle. It can be seen that the use of the bridge molecule 13 leads to a significant increase of the loading density. This results not only from the fact that a bridge molecule 13 can, on the ligand side, have several reactive organic groups 15. Within the scope of the present invention, it has been shown that an increase of the loading density can also be achieved when the bridge molecule has only one such group. This may well be due to the fact that, especially in the case of the use of very small carrier particles, the spatial conditions are less favorable when the ligand is coupled with its reactive group 17 directly on to the corresponding complementary organic group 12 of the silanization reagent 10.

Figure 3:
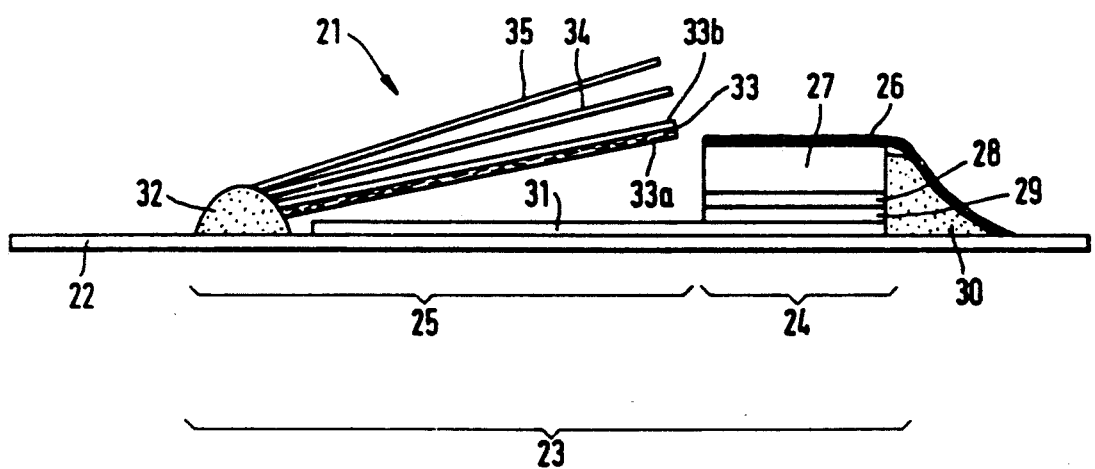
FIG. 3 illustrates in side view a test carrier according to the present invention.

The test carrier 21 illustrated in FIG. 3 is in the form of a test strip. However, it is a very sophisticated analysis system which is scarcely comparable with previously known test strips and especially with those used for carrying out immunological determinations.

On a base layer 22, there is present a test region, indicated in toto by 23, which extends over only a part of the length of the base layer 22. The test region 23 is subdivided into a sample application zone 24 and an evaluation zone 25.

In the sample application zone 24, one has a covering mesh 26, an erythrocyte separation layer 27 and two reagent layers 28 and 29 which are fixed to the base layer 22 with a melt adhesive strip 30.

A liquid transport layer 31 made of an absorbent material, which is also fixed with the melt adhesive strip 30, extends from the sample application zone 24 into the evaluation zone 25. Above the region of the liquid transport layer 31 which is not covered by the layers 26 to 29 are three layers 33-35 which are fixed with a melt adhesive strip 32 on to the base layer 22. These are fixed so that, without external pressure, they stand up obliquely from layer 22 and do not touch it. These are a test layer 33 with a ligand fixed according to the present invention, a third reagent layer 34 and a covering film 35.

The illustrated preferred test carrier is useful for carrying out immunological determinations which are based on the so-called IEMA principle.

If, for example, an antigen (Ag) contained in a sample is to be determined, then the analysis with the test carrier illustrated in FIG. 3 proceeds as follows:

A drop of blood (about 30 μl, e.g.) is applied above the erythrocyte separation layer to the covering mesh 26 and penetrates the erythrocyte separation layer 27, which can be made, for example, according to U.S. Pat. No. 4,477,575. The serum thus obtained penetrates into the layer 29.

The layer 29 contains an enzyme-labelled antibody (Ab) for the Ag which is in excess compared with the maximum Ag concentration in the sample. This antibody-enzyme conjugate (AbE) is dissolved by the serum. Complexes between AbE and Ag, then form which are designated by Ag-AbE. Since AbE is present in excess, upon adjustment of the equilibrium, free conjugate AbE remains.

It is the task of the layer 33 to remove this AbE, which would disturb the analysis, via immunological binding. Therefore, this layer may be referred to as an immunological separation layer. It contains the analyte or an analyte analogue in carrier-fixed form, which has been fixed using inorganic carrier particles.

After the expiration of a predetermined incubation time, in which the equilibrium has adjusted in the preceding reaction, pressure is exerted on the layers 33–35. This can take place manually or, as described, for example, in European Patent Specification No. 0,129,220, mechanically with the help of a component of the apparatus used. By means of the application of pressure, the immunological separation layer 33 comes into contact with the liquid transport layer 31 and the components contained therein pass into the layer 33. The non-complexed AbE thereby couples on to the fixed Ag, whereas the Ag-AbE complexes can further penetrate unhindered.

The reagent layer 34 contains a color-forming substrate for the labelling enzyme. When the liquid has reached the substrate, the enzyme of the unbound Ag-AbE complexes catalyzes the color forming reaction of the substrate. The speed of the color change is, therefore, a measure of the free complexes Ag-AbE which have reached the reagent layer 34. This is, in turn, a measure of the Ag contained in the sample. With regard to the course of an IEMA test on a test carrier, reference is additionally made to German Patent Application No. 36 38 654.

For the proper functioning of the test carrier according to FIG. 3, the construction and the action of the immunological separation layer 33 are of special importance. The color change in the substrate layer 34 is only a reproducable measure for the Ag concentration when the layer 33 provides for a complete separation of non-complexed AbE. If this does not occur, then the enzymatic activity in the region of the substrate layer 33 would be too high and the result would be falsified. Similar conditions have to be met in other immunological determinations. Therefore in many cases a ligand is to be present at maximum loading density.

The layer 33 preferably consists of a carrying fabric or fleece 33a with a coating 33b applied thereto, which is preferably made as a solution or dispersion of a film-forming organic synthetic resin with the addition of an opener in the form of corpuscular components, as has been explained hereinbefore in more detail. This fabric composite layer is produced by coating the film layer directly on the fabric or fleece, the viscosity of the film layer being so adjusted that it on the one hand, penetrates to some extent into the fabric but, on the other hand, remains preponderantly on one side of the fabric. In this regard, reference is made to U.S. Pat. No. 4,604,264.

Due to the unusually high loading density possible according to the present invention, the layer 33 has outstanding separation properties. All non-complexed AbE, upon penetration into the layer, is immediately bound to the fixed Ag so that the "disturbing" enzyme activity remains only in the region of the lower (i.e. facing the liquid transport layer 31) surface of the layer 33.

In this way, as described hereinbefore, only the Ag-AbE complexes pass to the substrate in the substrate layer 34. However, the substrate will usually be soluble and it is also possible that a part of the substrate 34 passes by diffusion to the lower surface of the layer 33 where the intercepted AbE is bound. In order to prevent a disturbance of the measurement, the layer contains a sufficient amount of pigment so that, in the case of visual evaluation or of evaluation with apparatus of the color change, such a disturbing color change cannot be detected from the upper side of the test carrier.

When, as carrier particles, inorganic particles are used, in many cases they already have pigment properties so that they fulfill the double function of a carrier for the carrier-fixed reagents and of an optical barrier. This is especially true for titanium dioxide. In this way, there is provided a separating layer which, even in the case of very small layer thickness of less than 200 $\mu$, meets all requirements.

The following Examples are given for the purpose of illustrating the present invention but are not limitative thereof.

EXAMPLE 1

Total thyroxine (T4) test 1.1. Construction and function of the test carrier

The construction and function of the test carrier is according to FIG. 3. In order to make possible the detection of the total thyroxine present in serum, liberation of the protein-bound T4 is necessary by means of an appropriate displacement reagent which is present in the first reagent layer 28.

1.2. Preparation of the separation layer 33

1.2.1. Aminosilanization of titanium dioxide (TiO$_2$-Si)

50 g. titanium dioxide (RN43, Dronos-Titan, Leverkusen, Federal Republic of Germany) are suspended in 1000 ml double distilled water and stirred with 10 ml 3-aminopropyltriethoxysilane (Sigma-Chemie, Deisenhofen, Federal Republic of Germany) for 2 hours at 75° C. with monitoring of the pH value (pH 3-4). Thereafter, filtering is carried out over a glass frit (G5), followed by washing up neutral pH with double distilled water.

1.2.2. Preparation of the bridge molecules (TiO$_2$-Si-Ga-Cc)

50 g. of silanized titanium dioxide (TiO$_2$-Si) are suspended in 250 ml glutardialdehyde solution (25% in water, Sigma-Chemie, Deisenhofen, Federal Republic of Germany) and stirred for 12 hours at pH 7.4. Thereafter, it is filtered off over a glass frit (G5), first washed with double distilled water and then with 0.5 M phosphate buffer (pH 7.6). The solid phase is taken up in 225 ml phosphate buffer and stirred for 12 hours with 25 ml Crotein-C (Cc) solution (10% in phosphate buffer, Cc from Croda, Nettetal, Federal Republic of Germany). For the complete reaction of the remaining free aldehyde groups, 50 g. of solid phase (washed in phosphate buffer) are stirred in 500 ml. 0.5 M phosphate buffer with 0.5 M glycine for 1 hour. After intensive washing with double distilled water, the sediment (about 50 g) is taken up in 450 ml borate buffer (pH 8.5) and stirred with 50 ml sodium cyanideborohydride solution (5% in borate buffer) for 15 minutes for the reduction of the Schiffs bases. Subsequently, it is filtered off over a glass frit (G5) and washed with phosphate buffer and double distilled water.

1.2.3. Coupling on a BOC-T4-hydroxysuccinimide ($TiO_2$-Si-GA-Cc-T4) as analyte analogue 10 g. $TiO_2$-Si-GA-Cc are suspended in 200 ml. 0.06 M $Na_2HPO_4$ (pH 8.8) and stirred in the dark with 170 ml. BOC-T4-hydroxysuccinimide solution (0.05% in dioxane) for 2 hours. Thereafter, washing is carried out with 0.06 M $Na_2HPO_4$/dioxane (10:8.5) and with double distilled water (several times) and the product is filtered off with suction.

1.2.4. Film coating on to fabric

A coating mass with the composition:

| | |
|---|---|
| Propiofan 70D (BASF, Ludwigshafen, Federal Republic of Germany) | 4 g. |
| Brij 35 (Serva, Heidelberg, Federal Republic of Germany) 15% solution in Gal buffer, composition: see below | 1 g. |
| Polyox WSR 301 (Union Carbide, New York, U.S.A. (2.5% in Gal buffer) | 5 g. |
| $TiO_2$—T4 matrix coupling (40% suspension in Gal buffer) | 30 g. |
| kieselguhr MW 25 | 9 g. |
| | 49 g. | is applied to a fabric PE 812 K6 (Schweizer Seidengazefabrik, Thal, Switzerland) with a wet film thickness of 35 μ and dried.

1.3. Preparation of the displacement reagent on the first reagent layer 28

200 mM T4 displacement reagent are dissolved in Gal buffer and impregnated on to tea bag paper (Schöller & Hösch, Gernsheim, Federal Republic of Germany). Gal buffer has the following composition:

| | |
|---|---|
| monopotassium dihydrogen phosphate | 10 mM |
| magnesium chloride | 5 mM |
| sodium chloride | 25 mM |
| pH | 7.0 |

1.4. Preparation of the second reagent layer 29 as conjugate layer

The impregnation was onto fabric PE 14 100 normal (Schweizer Seidengazefabrik, Thal, Switzerland). The impregnation solution has the following composition:

| | |
|---|---|
| Hepes | 50 mM |
| magnesium chloride | 5 mM |
| alpha-D-glucopyranosyl-alpha-D-glucopyranoside | 1% |
| Crotein C | 1% |
| <T4>-βGal conjugate | 80 U/ml. |
| pH | 6.6 |

1.5. Preparation of the third reagent layer 34 as substrate layer

The impregnation was onto fabric PE HE-1 (Schweizer Seidengazefabrik, Thal, Switzerland). The impregnation solution comprises chlorophenol red galactoside (CPRG) 20 mM in Gal buffer.

1.6 Results

30 μl amounts of sera with different total T4 concentrations are applied to test strips and measured at 567 nm in a "Reflotron" apparatus (Boehringer Mannheim GmbH), the following results being obtained:

| μg./dl. T4 | % remission after 1 minute |
|---|---|
| 0.55 | 52.25 |
| 6.65 | 44.51 |
| 10.00 | 38.52 |
| 20.90 | 31.48 |

The achievable gradation in the clinically relevant range of from 2.0 to 17.0 μg/dl permits a very precise measurement.

EXAMPLE 2

Theophylline test

2.1. Construction and function of the test carrier

As in Example 1 except that the first reagent layer 28 is omitted.

2.2. Preparation of the separation layer 33

2.2.1. Carboxysilanization of titanium dioxide ($TiO_2$-Si) for the production of coupling groups 500 ml double distilled water, adjusted to pH 5 with glacial acetic acid, are stirred for 2 hours at 75° C. with 10 ml. 3-triethoxysilylpropyl-succinic acid anhydride (Wacker-Chemie, München, Federal Republic of Germany) and 50 g. titanium dioxide, suspended in 200 ml. double distilled water. The product is then filtered with suction over a glass frit (G5) and washed several times with double distilled water.

2.2.2. Preparation of the bridge molecules ($TiO_2$-Si-Cc)

25 g. silanized titanium dioxide ($TiO_2$-Si) are suspended in 125 ml. double distilled water. 1.5 g. 1-Ethyl-3-(3-dimethylaminopropyl)-carbodiimide hydrochloride (Sigma-Chemie, Deisenhofen, Federal Republic of Germany) is added thereto at pH 4.5 and the reaction mixture stirred for 30 minutes at ambient temperature. Thereafter, 125 ml. 2% Crotein C (Cc) solution are added thereto and stirring is carried out for 12 hours. After the addition of a further 50 ml. of Cc solution, stirring is continued for a further 1 hour and then the product is filtered off with suction over a glass frit (G5) while washing several times with double distilled water.

2.2.3. Coupling of theophylline-polyhaptenhydroxy-succinimide ($TiO_2$-Si-Cc-polyTheo) as analyte analogue 15 g. $TiO_2$-Si-Cc are suspended in 75 ml. 0.1 M phosphate buffer (pH 8.7) and stirred for 12 hours with 150 mg. activated theophylline-polyhapten (poly-Theo-O-Su, dissolved in dimethyl sulphoxide). Thereafter, the product is filtered off with suction over a glass frit (G5), washed twice with dimethyl sulphoxide/double distilled water (1:1 v/v) and several times with double distilled water.

2.2.4. Film coating

The film coating takes place analogously to Example 1.

2.3. Preparation of the conjugate layer 29

<α-Theo>-βGal conjugate, dissolved in phosphate buffered saline with 1% Crotein C, is impregnated onto stencil paper (Schöller & Hösch, Gernsbach, Federal Republic of Germany) so that 1U enzyme activity/cm$^2$ is available.

2.4. Preparation of the substrate layer 34

This takes place as in Example 1.

2.5. Results

30 μl amounts of sera with different theophylline concentrations are applied to test carriers and measured at 567 nm on a "Reflotron" apparatus (Boehringer Mannheim GmbH), the following results being obtained:

| mg./dl. theophylline | % remission after 2 minutes |
| --- | --- |
| 0 | 55.10 |
| 1.0 | 38.87 |
| 1.5 | 33.56 |
| 3.1 | 22.84 |

The achievable gradation in the clinically relevant range of from 1 to 3 mg./dl. permits very precise measurements.

It will be understood that the specification and examples are illustrative but not limitative of the present invention and that other embodiments within the spirit and scope of the invention will suggest themselves to those skilled in the art.

We claim:

1. Test carrier for analysis of a component in a sample liquid by means of a specific binding reaction of a first and a second binding partner contained in said test carrier comprising: a plurality of test layers, wherein at least of one said test layers is a separation layer which is positioned between an upstream layer and a downstream indicator layer constructed so as to detect the component in the liquid sample such that said sample liquid penetrates through said separation layer when said upstream layer, said separation and said downstream layer are in fluid contact, said upstream layer containing a soluble conjugate of a labelling agent and a first binding partner of said specific binding reaction for being dissolved by said sample liquid and forming labeled complexes with a component of said sample liquid wherein said labeled complexes are floating in said sample liquid and being indicative of said analysis, said separation layer having a porous three dimensional structure and containing said second binding partner of said specific binding reaction fixed to said separation layer for removing excess conjugate from the sample liquid that penetrates therethrough wherein said separation layer contains carrier particles having a surface and consisting of inorganic material having pigment properties, and wherein said particles are fixed in said porous three dimensional structure, and wherein said second binding partner is fixed to said carrier particles by covalent binding to a reactive organic coupling group on the surface of said carrier particles.

2. Test carrier of claim 1 wherein said covalent binding comprises a bridge molecule having two ends and being covalently bound to said ligand near one end and to said reactive coupling group near the other end.

3. Test carrier of claim 1, wherein said reactive organic coupling group is generated on said carrier particle by a silanizing group.

4. Test carrier of claim 1, wherein said carrier particles have an average particle diameter of from 0.2 to about 1 u.

5. Test carrier of claim 1, wherein said carrier particles are titanium dioxide particles.

6. Test carrier of claim 1, wherein said test layer is a film produced from a solution or a dispersion of a film forming, organic, synthetic resin and contains particulate components as a film opener.

7. Test carrier of claim 6, wherein said film opener comprises inorganic particles.

8. Test carrier of claim 7, wherein said inorganic particles are silicon dioxide.

9. Test carrier of claim 7, wherein said inorganic particles have an average particle diameter of at least about 5 u.

10. Test carrier of claim 6, wherein said film opener comprises diatomaceous earth.

11. Test carrier of claim 6, wherein said film forming organic synthetic resin amounts to no more than 25% by the weight of carrier particles and film opener.

12. Test carrier of claim 6. wherein said carrier particles and film opener are present in a weight ratio of from 2:1 to 1:2.

13. Test carrier of claim 1, wherein said separation layer comprises a coating and a material selected from the group consisting of fabric or fleece in which said coating partly penetrates but remains preponderantly on one side thereof.

14. Method for determining a component of a liquid sample comprising contacting said liquid sample to a test carrier of claim 1 and determining said component thereafter.

* * * * *

UNITED STATES PATENT AND TRADEMARK OFFICE
CERTIFICATE OF CORRECTION

PATENT NO. : 5,162,238
DATED : November 10, 1992
INVENTOR(S) : Eikmeier et al.

It is certified that error appears in the above-identified patent and that said Letters Patent is hereby corrected as shown below:

Col. 1, line 6, "useful of a sample" should read --useful for the analysis of a sample--.

Signed and Sealed this

Fifteenth Day of March, 1994

Attest:

BRUCE LEHMAN

Attesting Officer   Commissioner of Patents and Trademarks